(12) United States Patent
Borok et al.

(10) Patent No.: US 7,601,345 B2
(45) Date of Patent: Oct. 13, 2009

(54) LENTIVIRUS VECTORS FOR GENE TRANSFER TO ALVEOLAR EPITHELIAL CELLS

(75) Inventors: Zea Borok, Los Angeles, CA (US); Nori Kasahara, Los Angeles, CA (US); Edward Crandall, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/716,173

(22) Filed: Mar. 9, 2007

(65) Prior Publication Data

US 2008/0081365 A1    Apr. 3, 2008

Related U.S. Application Data

(62) Division of application No. 10/119,499, filed on Apr. 9, 2002, now Pat. No. 7,211,247.

(60) Provisional application No. 60/282,556, filed on Apr. 9, 2001.

(51) Int. Cl.
*A01N 63/00* (2006.01)
*A61K 48/00* (2006.01)
*C12N 15/00* (2006.01)
*C12N 15/63* (2006.01)

(52) U.S. Cl. .................. 424/93.21; 424/93.2; 424/93.6; 435/320.1; 435/455

(58) Field of Classification Search ................ 424/93.2, 424/93.21, 93.6; 435/320.1, 455
See application file for complete search history.

(56) References Cited

U.S. PATENT DOCUMENTS

| 5,948,681 A | 9/1999 | Scanlin |
| 6,277,633 B1 | 8/2001 | Olsen |

OTHER PUBLICATIONS

Albelda, S. M., R. Wiewrodt, and J. B. Zuckerman. 2000. Gene therapy for lung disease: hype or hope? Ann. Intern. Med. 132:649-660.
Bertalanffy F. D. 1964. Respiratory tissue: structure, histophysiology, cyto-dynamics. II. New approaches and interpretations. Int. Rev. Cytol. 17:213-297.
Borok, Z., S. I. Danto, S. M. Zabski, and E. D. Crandall. 1994. Defined medium for primary culture de novo of adult rat alveolar epithelial cells. In Vitro Cell Dev. Biol. Anim. 30A:99-104.
Bowden, D. H., E. Davies, and J. P. Wyatt. 1968. Cytodynamics of pulmonary alveolar cells in the mouse. Arch. Pathol. 86:667-670.
Brigham, K. L., and A. A. Stecenko. 2000. Gene therapy for acute lung injury. Intensive Care Med. 26:S119-S123.
Cheek, J. M., M. J. Evans, and E. D. Crandall. 1989. Type I cell-like morphology in tight alveolar epithelial monolayers. Exp. Cell Res. 184:375-387.

Cheek, J. M., K. J. Kim, and E. D. Crandall. 1989. Tight monolayers of rat alveolar epithelial cells: bioelectric properties and active sodium transport. Am. J. Physiol. 256:C688-C693.
Chirmule, N., K. Propert, S. Magosin, Y. Qian, R Qian, and J. Wilson. 1999. Immune responses to adenovirus and adeno-associated virus in humans. Gene Ther. 6:1574- 1583.
Christensen, P. J., S. Kim, R. H. Simon, G. B. Toews, and R D. Paine. 1993. Differentiation-related expression of ICAM-1 by rat alveolar epithelial cells. Am. J. Respir. Cell Mot. Biol. 8:9-15.
Danto, S. I., S. M. Zabski, and E. D. Crandall. 1992. Reactivity of alveolar epithelial cells in primary culture with type I cell monoclonal antibodies. Am. J. Respir. Cell Mol. Biol. 6:296-306.
Dobbs, L. G., R. Gonzalez, and M. C. Williams. 1986. An improved method for isolating type II cells in high yield and purity. Am. Rev. Respir. Dis. 134:141-145.
Dong, J. Y., D. Wang, F. W. Van Ginkel, D. W. Pascual, and R A. Frizzell. 1996. Systematic analysis of repeated gene delivery into animal lungs with a recombinant adenovirus vector. Hum. Gene Ther. 7:319-331.
Duan, D., Y. Vue, Z. Yan, J. Yang, and J. F. Engelhardt. 2000. Endosomal processing limits gene transfer to polarized airway epithelia by adeno-associated virus. J. Clin. Investig. 105:1573-1587.
Engelhardt, J. F., J. R. Yankaskas, and J. M. Wilson. 1992. In vivo retroviral gene transfer into human bronchial epithelia of xenografts. J. Clin. Investig. 90:2598-2607.
Factor, P., F. Saldias, K. Ridge, V. Dumasius, J. Zabner, H. A. Jaffe, G. Blanco, M. Barnard, R. Mercer, R. Perrin, and J. I. Sznajder. 1998. Augmentation of lung liquid clearance via adenovirus-mediated transfer of a Na,K-ATPase beta 1 subunit gene. J. Clin. Investig. 102:1421-1430.
Flotte, T. R, S. A. Afione, C. Conrad, S. A. McGrath, R. Solow, H. Oka, P. L. Zeitlin, W. B. Guggino, and B. J. Carter. 1993. Stable in vivo expression of the cystic fibrosis transmembrane conductance regulator with an adeno-associated virus vector. Proc. Natl. Acad. Sci. USA 90:10613-10617.
Flotte, T. R, S. A. Afione, and P. L. Zeitlin. 1994. Adeno-associated virus vector gene expression occurs in nondividing cells in the absence of vector DNA integration. Am. J. Respir. Cell Mol. Biol. 11:517-521.
Fuller, S., C. H. von Bonsdorff, and K. Simons. 1984. Vesicular stomatitis virus infects and matures only through the basolateral surface of the polarized epithelial cell line, MDCK. Cell 38:65-77.

(Continued)

*Primary Examiner*—Shin-Lin Chen
(74) *Attorney, Agent, or Firm*—Bingham McCutchen LLP

(57) ABSTRACT

The present invention demonstrates that VSV-G-pseudotyped lentivirus vectors efficiently transduce AEC in primary culture and in vivo with transduction favored by virus application from the apical side. Transduction efficiency in AEC increased with increasing MOI and greatly exceeded that achieved with a similarly pseudotyped MLV retrovirus vector. The present invention also demonstrates the successful in vivo transfer of genes through lentivirus vector transduction. Mammals injected with lentivirus vector via the trachea expressed the reporter protein in alveolar epithelial cells within 48 to 72 hours after infection.

2 Claims, 6 Drawing Sheets

OTHER PUBLICATIONS

Goldman, M. J., P. S. Lee, J. S. Yang, and J. M. Wilson. 1997. Lentivirus vectors for gene therapy of cystic fibrosis. Hum. Gene Ther. 8:2261-2268.

Grimm, D., and J. A. Kleinschmidt. 1999. Progress in adeno-associated virus type 2 vector production: promises and prospects for clinical use. Hum. Gene Ther. 10:2445-2450.

Johnson, L. G., J. C. Olsen, L. Naldini, and R C. Boucher. 2000. Pseudotyped human lentivirus vector-mediated gene transfer to airway epithelia in vivo. Gene Ther. 7:568-574.

Kaartinen, L., P. Nettesheim, K. B. Adler, and S. H. Randell. 1993. Rat tracheal epithelial cell differentiation in vitro. In Vitro Cell Dev. Biol. Anim. 29A:481-492.

Kafri, T., U. Blomer, D. A. Peterson, F. H. Gage, and I. M. Verma. 1997. Sustained expression of genes delivered directly into liver and muscle by lentivirus vectors. Nat. Genet. 17:314-317.

Kim, K. J., J. M. Cheek, and E. D. Crandall. 1991. Contribution of active $Na^+$ and $Cl^-$ fluxes to net ion transport by alveolar epithelium. Respir. Physiol. 85:245-256.

Kobinger, G. P., D. J. Weiner, Q.C. Yu, and J. M. Wilson. 2001. Filovirus-pseudotyped lentivirus vector can efficiently and stably transduce airway epithelia in vivo. Nat. Biotechnol. 19:225-230.

Leslie, C. C., K. McCormick-Shannon, J. L. Cook, and R. J. Mason. 1985. Macrophages stimulate DNA synthesis in rat alveolar type II cells. Am. Rev. Respir. Dis. 132:1246-1252.

Leslie, C. C., K. McCormick-Shannon, P. C. Robinson, and R. J. Mason. 1985. Stimulation of DNA synthesis in cultured rat alveolar type II cells. Exp. Lung Res. 8:53-66.

Leslie, C. C., K. McCormick-Shannon, J. M. Shannon, B. Garrick, D. Damm, J. A. Abraham, and R J. Mason. 1997. Heparin-binding EGF-like growth factor is a mitogen for rat alveolar type ll cells. Am. J. Respir. Cell Mol. Biol. 16:379-387.

Mason, R. J., S. R. Walker, B. A. Shields, J. E. Henson, and M. C. Williams. 1985. Identification of rat alveolar type ll epithelial cells with a tannic acid and polychrome stain. Am. Rev. Respir. Dis. 131:786-788.

Miller, A. D. 1996. Cell-surface receptors for retroviruses and implications for gene transfer. Proc. Natl. Acad. Sci. USA 93:11407-11413.

Miller, D. G., M. A. Adam, and A. D. Miller. 1990. Gene transfer by retrovirus vectors occurs only in cells that are actively replicating at the time of infection. Mol. Cell. Biol. 10:4239-4242.

Miyoshi, H., U. Blomer, M. Takahashi, F. H. Gage, and I. M. Verma. 1998. Development of a self-inactivating lentivirus vector. J. Virol. 72:8150-8157.

Naldini, L. 1998. Lentiviruses as gene transfer agents for delivery to non-dividing cells. Curr. Opin. Biotechnol. 9:457-463.

Naldini, L., U. Blomer, P. Gallay, D. Ory, R. Mulligan, F. H. Gage, I. M. Verma, and D. Trono. 1996. In vivo gene delivery and stable transduction of nondividing cells by a lentivirus vector. Science 272:263-267.

Ostrowski, L. E., S. H. Randell, A. B. Clark, T. E. Gray, and P. Nettesheim. 1995. Ciliogenesis of rat tracheal epithelial cells in vitro. Methods Cell Biol. 47:57-63.

Pickles, R. J., D. McCarty, H. Matsui, P. J. Hart, S. H. Randell, and R C. Boucher. 1998. Limited entry of adenovirus vectors into well-differentiated airway epithelium' is responsible for inefficient gene transfer. J. Virol. 72: 6014-6023.

Polonovsky, V., and P. B. Bitterman. 1997. Regulation of cell population size, p. 133-144. In J. B. West and R. G. Crystal (ed.), the lung: scientific foundations, 2nd ed., vol. 1. Lippincott-Raven Publishers, Philadelphia, Pa.

Reiser, J. 2000. Production and concentration of pseudotyped HIV-1-based gene transfer vectors. Gene Ther. 7:910-913.

Russo, R M., R. L. Lohman, and E. D. Crandall. 1992. Evidence for amiloride-sensitive sodium channels in alveolar epithelial cells. Am. J. Physiol. 262:L405- L411.

Sakoda, T., N. Kasahara, Y. Hamamori, and L. Kedes. 1999. A high-titer lentiviral production system mediates efficient transduction of differentiated cells including beating cardiac myocytes. J. Mol. Cell. Cardiol. 31:2037-2047.

Schlegel, R, T. S. Tralka, M. C. Willingham, and I. Pastan. 1983. Inhibition of VSV binding and infectivity by phosphatidylserine: is phosphatidylserine a VSV-binding site? Cell 32:639-646.

Seppen, J., S. C. Barry, J. H. Klinkspoor, L. J. Katen, S. P. Lee, J. V. Garcia, and W. R Osborne. 2000. Apical gene transfer into quiescent human and canine polarized intestinal epithelial cells by lentivirus vectors. J. Virol. 74:7642-7645.

Sisson, T. H., N. Hattori, Y. Xu, and R. H. Simon. 1999. Treatment of bleomycin-induced pulmonary fibrosis by transfer of urokinase-type plasminogen activator genes. Hum. Gene Ther. 10:2315-2323.

Soneoka, Y., P. M. Cannon, E. E. Ramsdale, J. C. Griffiths, G. Romano, S. M. Kingsman, and A. J. Kingsman. 1995. A transient three-plasmid expression system for the production of high titer retroviral vectors. Nucleic Acids Res. 23:628-633.

Trono, D. 2000. Lentivirus vectors: turning a deadly foe into a therapeutic agent. Gene Ther. 7:20-23.

Uhal, B. D. 1997. Cell cycle kinetics in the alveolar epithelium. Am. J. Physiol. 272:L1031-L1045.

Uhal, B. D., and M. D. Etter. 1993. Type II pneumocyte hypertrophy without activation of surfactant biosynthesis after partial pneumonectomy. Am. J. Physiol. 264:L153-L159.

Uhal, B. D., and D. E. Rannels. 1991. DNA distribution analysis of type II pneumocytes by laser flow cytometry: technical considerations. Am. J. Physiol. 261:L296-L306.

Walters, R W., T. Grunst, J. M. Bergelson, R. W. Finberg, M. J. Welsh, and J. Zabner. 1999. Basolateral localization of fiber receptors limits adenovirus infection from the apical surface of airway epithelia. J. Biol. Chem. 274:10219-10226.

G., B. L. Davidson, P. Melchert, V. A. Slepushkin, H. H. van Es, M. Bodner, D. J. Jolly, and P. B. McCray. 1998. Influence of cell polarity on retrovirus-mediated gene transfer to differentiated human airway epithelia. J. Virol. 72:9818-9826.

Wang, G., V. Slepushkin, J. Zabner, S. Keshavjee, J. C. Johnston, S. L. Sauter, D. J. Jolly, T. W. Dubensky, Jr., B. L. Davidson, and P. B. McCray, Jr. 1999. Feline immunodeficiency virus vectors persistently transduce nondividing airway epithelia and correct the cystic fibrosis defect. J. Clin. Investig. 104:R55-R62.

Wang, G., V. A. Slepushkin, M. Bodner, J. Zabner, H. H. van Es, P. Thomas, D. J. Jolly, B. L. Davidson, and P. B. McCray. 1999. Keratinocyte growth factor induced epithelial proliferation facilitates retroviral-mediated gene transfer to distal lung epithelia in vivo. J. Gene Med. 1:22-30.

Wang, G., J. Zabner, C. Deering, J. Launspach, J. Shao, M. Bodner, D. J. Jolly, B. L. Davidson, and P. B. McCray, Jr. 2000. Increasing epithelial junction permeability enhances gene transfer to airway epithelia in vivo. Am. J. Respir. Cell Mol. Biol. 22:129-138.

Welsh, M. J. 1999. Gene transfer for cystic fibrosis. J. Clin. Investig. 104:1165-1166.

Yang, Y., Q. Li, H. C. Ertl, and J. M. Wilson. 1995. Cellular and humoral immune responses to viral antigens create barriers to lung-directed gene therapy with recombinant adenoviruses. J. Virol. 69:2004-2015.

Zabner, J. 1997. Cationic lipids used in gene transfer. Adv. Drug Deliv. Rev. 27:17-28.

Zufferey, R., T. Dull, R. J. Mandel, A. Bukovsky, D. Quiroz, L. Naldini, and D. Trono. 1998. Self-inactivating lentivirus vector for safe and efficient in vivo gene delivery. J. Virol. 72:9873-9880.

Zufferey, R., D. Nagy, R J. Mandel, L. Naldini, and D. Trono. 1997. Multiply attenuated lentivirus vector achieves efficient gene delivery in vivo. Nat. Biotechnol. 15:871-875.

Blomer et al. 1997. *Highly efficient and sustained gene transfer in adult neurons with a lentivirus vector*. J. Virol. 71:6641-6649.

Naldini et al. 1996. *In vivo gene delivery and stable transduction of nondividing cells by a lentiviral vector*. Science 272:263-267.

Naldini et al. 1996. *Efficient transfer, integration and sustained long-term expression of the transgene in adult rat brains injected with a lentiviral vector*. Proc. Natl. Acad. Sci. USA 93:11382-11388.

Kafri et al., 1997. *Sustained expression of genes delivered directly into liver and muscle by lentiviral vectors*. Nat. Genet. 17:314-317.

Bals et al., 1999. *Transduction of well-differentiated airway epithelium by recombinant adeno-associated virus is limited by vector entry*. J. Virol. 73:6-85- 6088.

Coyne et al., 2000. *Enhanced epithelial gene transfer by modulation of tight junctions with sodium caprate*. Am J Respir Cell Mol Biol. 23:602-9.

Johnson et al., 2000, *Pseudotyped human lentiviral vector-mediated gene transfer to aiway epithelia in vivo.* Gene Ther. 2000, Apr;7(7)568-74.

11 Copreni et al., *Lentivirus-Mediated Gene Transfer to the Respiratory Epithelium: a Promising Approach to Gene Therapy of Cystic Fibrosis*, Gene Therapy S67, S72 (2004).

1 Wang et al., *Keratinocyte Growth Factor Induced Epithelial Prliferation Facilitates Retroviral-Mediated Gene Transfer to Distal Lun Epithelia* in vivo, J. Gen Med. 22, 27 and Fig. 6 (1999).

Williams 2003, Annu Rev. Phsiol; 65;669-95.

Castranova et al., 1988. *The alveolar type II epithelial cell: a multifunctional pneumocyte*. Toxicol Appl Pharmacol. 93: 472-83.

Harboe-Schmidt et al., Mar. 15, 2000 (FASEB Journal, Vol. 14, No. 4, pp. A650).

Deonarain (1998, Expert Opin. Ther. Pat., Vol. 8, pp. 53-69).

Verma (Sept. 1997, Nature, Vol. 389, pp. 239-42).

Eck et al., 1996 (Goodman & Gilman's the Pharmacological Basis of Therapeutics, McGraw-Hill, New York pp. 77-101).

Pellinen et al., 2004 (International Journal of Oncology, Vol. 25, p. 1753-1762).

Isabel P Neuringer and Scott H Randell 2004. *Stem cells and reapir of lung injuries*. Respiratory Research, 5:6-15.

Lin, A, Kasahara, N, etal. Human Gene Tehrapy, 12:323-332, 2001.

N. Srinivasakaumar, "HIV-1 Vector Systems", Somatic Cell and Molecular Genetics (2001):26:(1-6), 51-81.

Dariusz C. Gorecki, "Propsects and Problems of Gene Therapy: An Update", Expert Opin. Emerging Drugs 6(2):187-194 (2001).

Pandya S., et al.: Lentivirus and foamy virus vectors: novel gene therapy tools. Exp. Opin. Biol. Ther. (2001) 1:17-40.

Kobinger GP, et al.: "Filovirus-pseudotyped lentiviral vector can efficiently and stably transducer airway epithelia in vivo." Nat. Biotechnol. (2001) 19:225-230.

Guenechea et al., "Transduction of Human Cd34+CD38-Bone Marrow and Cord Blood-Derived SCID Repopulating Cells with Third-Generation Lentiviral Vectors", Molecular Therapy (2000):1(6):566-573.

I. Hamaguchi et al; *Notes: Lentivirus Vector Gene Expression During ES Cell-Derived Hematopoietic Development in Vitro*; Aug. 19, 2000; pp. 10778-10784.

G.L. Buchschacher, Jr., et al; *Blood: Development of Lentiviral Vectors for Gene Therapy for Human Diseases*; Apr. 15, 2000; 7 pages.

S. Barrette et al ; *Blood: Lentivirus-Based Vectores Transduce Mouse Hematopoietic Stem Cells With Similar Efficiency to Moloney Murine Leukemia Virus-Based Vectors*; Nov. 15, 2000; pp. 3384-3391.

LENTIVIRUS VECTORS FOR GENE TRANSFER TO ALVEOLAR EPITHELIAL CELLS

CROSS-REFERENCE TO RELATED APPLICATIONS

This application is a Divisional of U.S. patent application Ser. No. 10/119,499, filed Apr. 9, 2002, now U.S. Pat. No. 7,211,247, which claims the benefit of U.S. Provisional Application No. 60/282,556, filed Apr. 9, 2001, the entire disclosure of which is hereby incorporated by reference in its entirety for all purposes.

STATEMENT REGARDING FEDERALLY SPONSORED RESEARCH

This invention was made without federal government support.

FIELD OF THE INVENTION

This invention relates to gene transfer. More particularly, this invention relates to the transduction of in vitro and in vivo alveolar epithelial cells by lentivirus vectors in which the virus is applied to the apical surface of the cell.

BACKGROUND OF THE INVENTION

Gene transfer to the alveolar epithelium is an attractive therapeutic approach for a number of acute and chronic acquired lung diseases, including pulmonary inflammation, pulmonary edema, acute lung injury (ALI), the acute respiratory distress syndrome (ARDS), and pulmonary fibrosis (1, 5, 15, 43). In addition, due to its large surface area and proximity to the vascular endothelium, the alveolar epithelium represents a desirable target for delivery of therapeutic genes encoding secreted proteins. However, in contrast to the large number of studies that have utilized a variety of vectors to achieve gene transfer to tracheal and bronchial epithelium in the upper airways, particularly in the context of gene therapy for cystic fibrosis (54), relatively few studies have examined gene transfer into the alveolar epithelium of the distal respiratory tract.

Non-viral strategies for delivery of exogenous DNA to the lung have been limited by low efficiency of transduction (56). Of the various vectors that have been evaluated for gene therapy thus far, each exhibits characteristic disadvantages, and none has proven effective in achieving efficient, long-term expression in the distal respiratory tract. Due to the relative quiescence of the cells that constitute the alveolar epithelium, viral vectors must be able to efficiently transduce cells that are not actively dividing. In this regard, adenoviral vectors have been shown to effectively transduce the alveolar epithelium (15). However, use of these vectors in vivo has been limited by immune responses, which can be especially problematic in the lung alveoli due to the potential for inducing serious pulmonary inflammation. In any event, use of this non-integrating vector system would also require repeated viral administration to achieve long-term gene expression (12). Adeno-associated virus (AAV) vectors show episomal expression and eventual integration following cell division and have been used for gene delivery to the distal respiratory tract (16, 17); however, their use has been limited by low packaging capacity and difficulty obtaining high titer preparations (20). Repeated administration of AAV vectors has been limited by the development of neutralizing antibodies (8). Thus, investigation of alternative vectors, such as retroviruses, for gene delivery to the alveolar epithelium is warranted.

Two types of retrovirus vectors, murine leukemia virus—(MLV) and lentivirus-based, have been tested for their efficiency in transducing alveolar epithelial cells ("AEC"). Under normal in vivo conditions, the cells that constitute the alveolar epithelium undergo very low rates of proliferation (2, 4, 46, 47). The efficiency of standard MLV-based retroviruses for gene transfer to the adult alveolar epithelium is therefore predictably inefficient (14, 50). This limitation has been partially overcome by inducing cell proliferation with growth factors, but overall transduction efficiency is still quite low. Newer lentivirus vectors, however, have recently been shown to transduce several non-dividing cell types including neuronal cells, myocytes, liver cells and tracheal epithelial cells, with long term persistence of transgene expression (21, 23, 34, 40).

Pseudotyping of the lentivirus with different envelope proteins has expanded the range of host cells that can be transduced by lentivirus vectors, and has also allowed the virus to be easily concentrated to high titers, especially when pseudotyped with the vesicular stomatitis virus envelope glycoprotein (VSV-G) (38). Lentivirus vectors would therefore appear to be ideally suited for gene transfer to the relatively quiescent cells of the alveolar epithelium. However, the lack of a well-characterized virus receptor and the polarized nature of its distribution makes transfection efficiency in different cell types unpredictable.

Studies to date have focused on lentivirus-based gene transfer to the tracheal or bronchial epithelium of the proximal airways. In polarized, well-differentiated airway epithelia, only minimal transduction by VSV-G pseudotyped vectors introduced from the apical surface (the only directly accessible surface in vivo) has been observed. The use of lentivirus vectors for transduction of adult alveolar epithelial cells in the distal respiratory tract has not been evaluated to date. In particular, whether the polarized cells that constitute the alveolar epithelium present a similar barrier to apical transduction by lentivirus has not been explored.

Based on the 1984 paper by Fuller et al., it was widely believed in the art that receptors for VSV-G were exclusively located on the basolateral cell surface (41). Because only the apical surface is accessible in AEC in vivo, it was believed that it would be futile to use VSV-G pseudotyped lentivirus to transduce these cells.

The present invention overcomes these hurdles and provides a composition and method for highly efficient transduction of AEC from the apical surface using the lentivirus vector.

SUMMARY OF THE INVENTION

The present invention provides a composition and method for using lentivirus vectors for gene transfer to alveolar epithelial cells applied to the apical surface. It is an objective of this invention to use lentivirus vectors to deliver therapeutic genes encoding secreted proteins to the alveolar epithelium and systemically via the alveolar epithelium.

It is a further objective of this invention to increase the efficiency of transduction of exogenous DNA to the lung.

It is another objective of this invention to achieve efficient, long-term gene expression in the distal respiratory tract.

It is also an objective of this invention to transduce the alveolar epithelium without inducing serious pulmonary inflammation or developing neutralizing antibodies.

It is yet another objective of this invention to deliver genes to the distal respiratory tract using vectors with a high packaging capacity.

It is a further objective of this invention to use lentivirus with different envelope proteins in order to concentrate the virus to high titers.

It is another objective of this invention to pseudotype the lentivirus with vesicular stomatitis virus envelope glycoprotein to easily concentrate the virus in high titers.

It is also an objective of this invention to develop therapies for acute and chronic acquired lung diseases, including pulmonary inflammation, pulmonary edema, acute lung injury/the acute respiratory distress syndrome, and pulmonary fibrosis.

It is a further objective of this invention to use the alveolar epithelium to produce and deliver drug therapies systemically in vivo.

SIN pRRLhCMVGFP lentivirus vectors were used to produce infectious particles by co-transfection of gag-pol pCMVΔR8.91 and pMD.G (for VSV-G envelope) into 293T cells.

Figure 2:
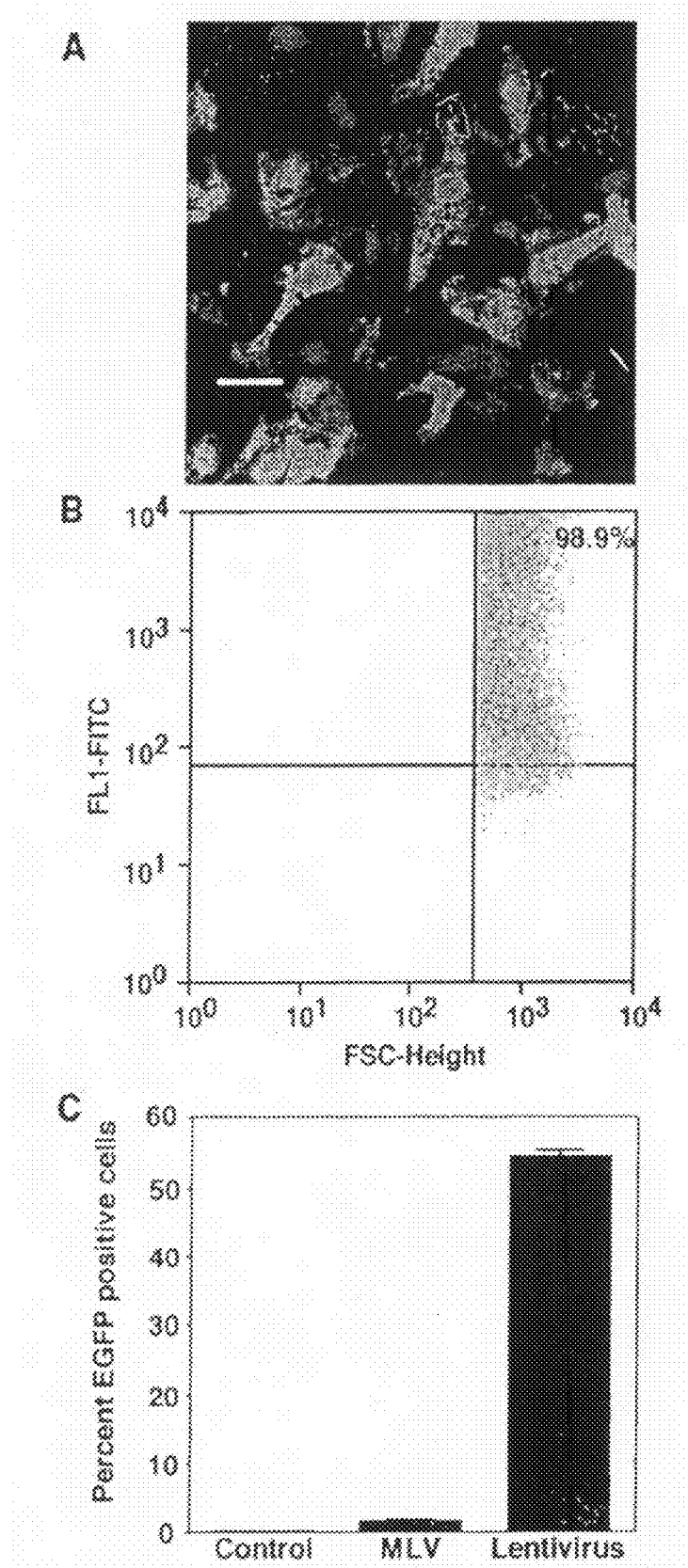

FIG. 2. Transduction of AEC with VSV-G pseudotyped lentivirus.
  (A) AEC in primary culture on chamber slides were transduced with VSV-G pseudotyped lentivirus at an MOI of 10. Confocal microscopy from a representative experiment three days post-transduction demonstrates strong expression of EGFP in a majority of cells.
  (B) AEC grown on plastic tissue culture dishes were transduced with VSV-G pseudotyped lentivirus. Representative FACS analysis at 72 hours after infection demonstrates 99% GFP-positive cells at an MOI of 50.
  (C) Transduction of AEC grown on plastic is ~30-fold greater for VSV-G pseudotyped lentivirus than VSV-G pseudotyped MLV-based virus at a comparable titer.

Figure 3:
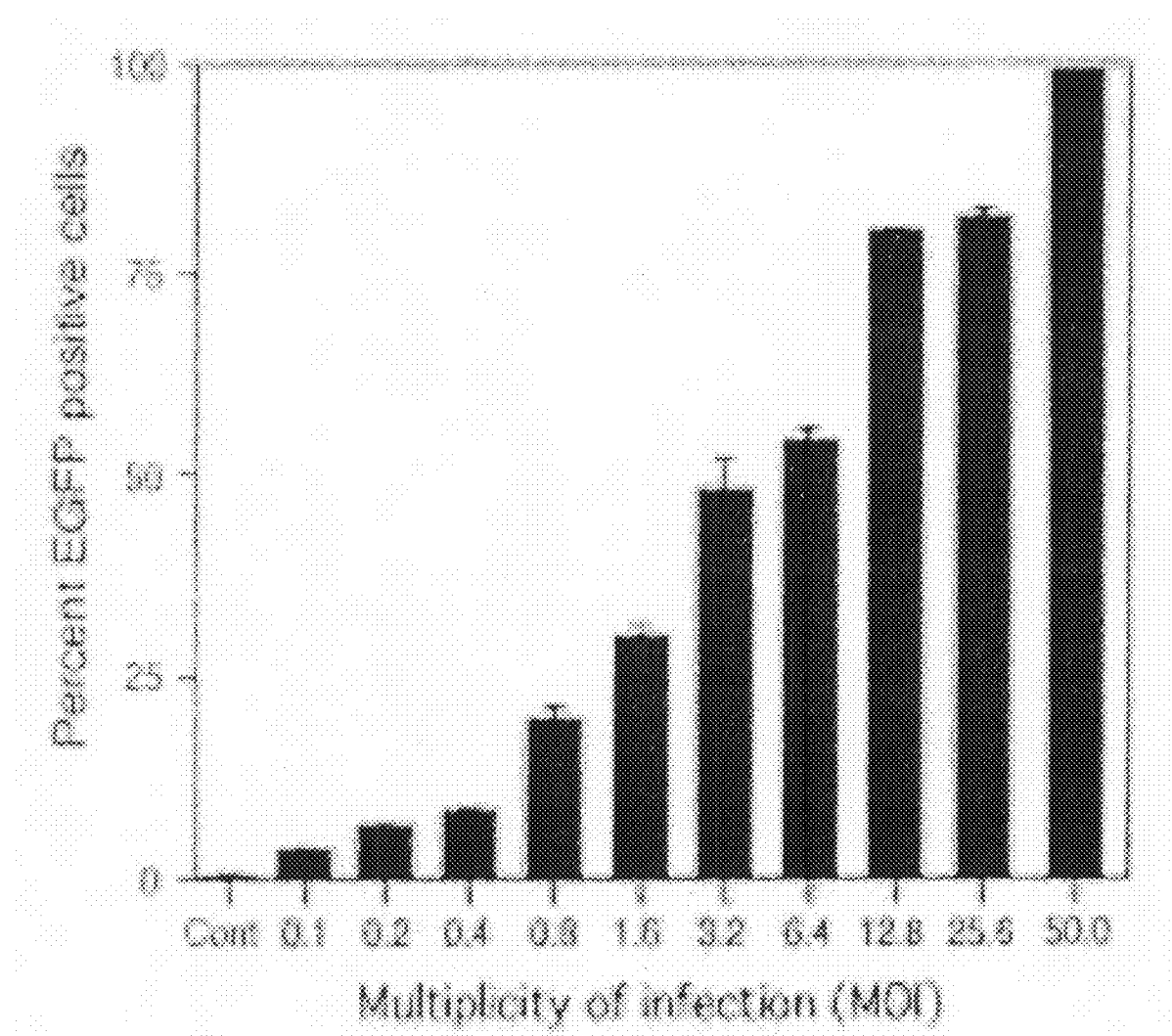

FIG. 3. Effect of varying MOIs on the efficiency of transduction of AEC with VSV-G pseudotyped lentivirus vectors.

Alveolar epithelial cells grown on plastic were transduced with VSV-G pseudotyped lentivirus previously titered on 293T cells ($1-2\times10^8$ IU/ml). The transduction efficiency ranged from 4% to 99% EGFP-positive cells with MOIs from 0.1 to 50, respectively.

Figure 4:
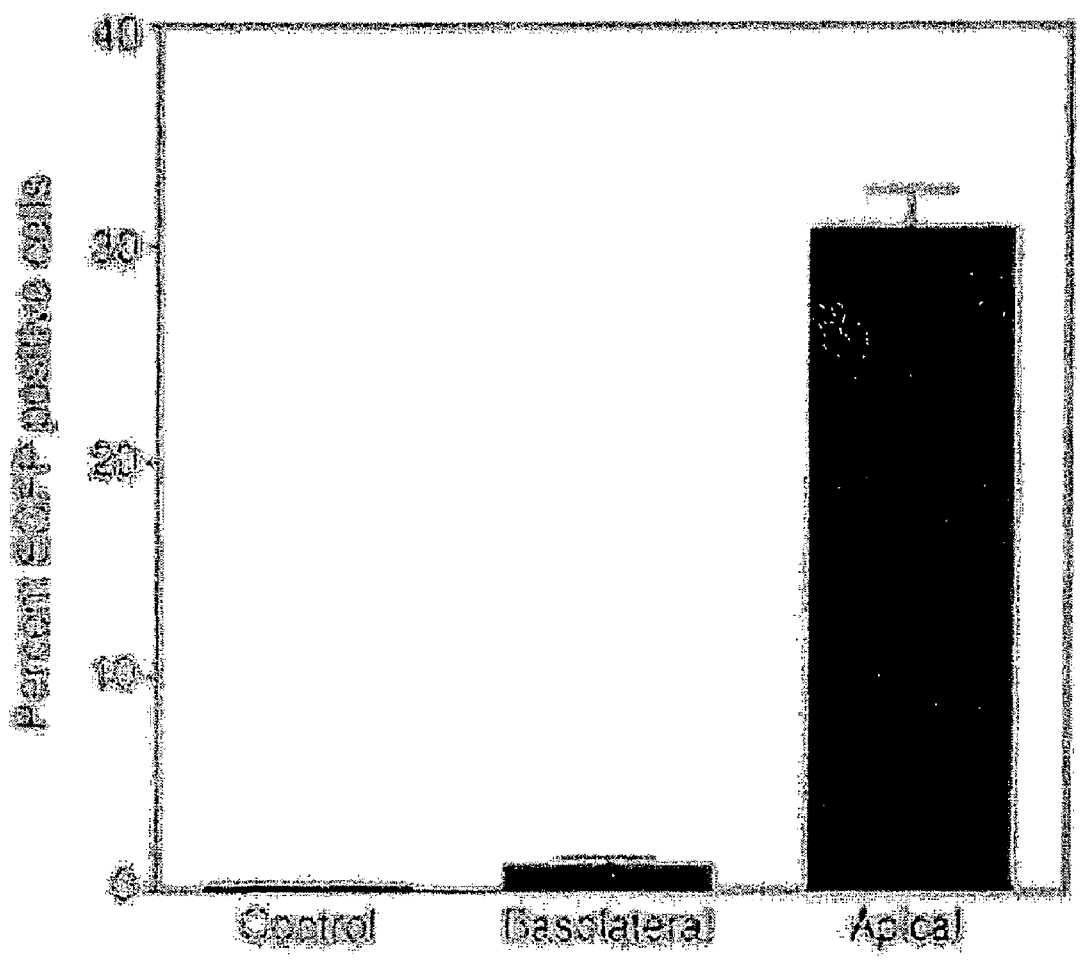

FIG. 4. Polarized transduction of AEC by lentivirus vectors.

AEC monolayers on polycarbonate filters were infected with VSV-G pseudotyped lentivirus vectors (MOI=10) from either the apical or basolateral surface and analyzed by FACS at three days post-transduction. VSV-G pseudotyped lentivirus vectors infected polarized AEC monolayers more efficiently from the apical surface (apical:basolateral, 25:1).

Figure 5:
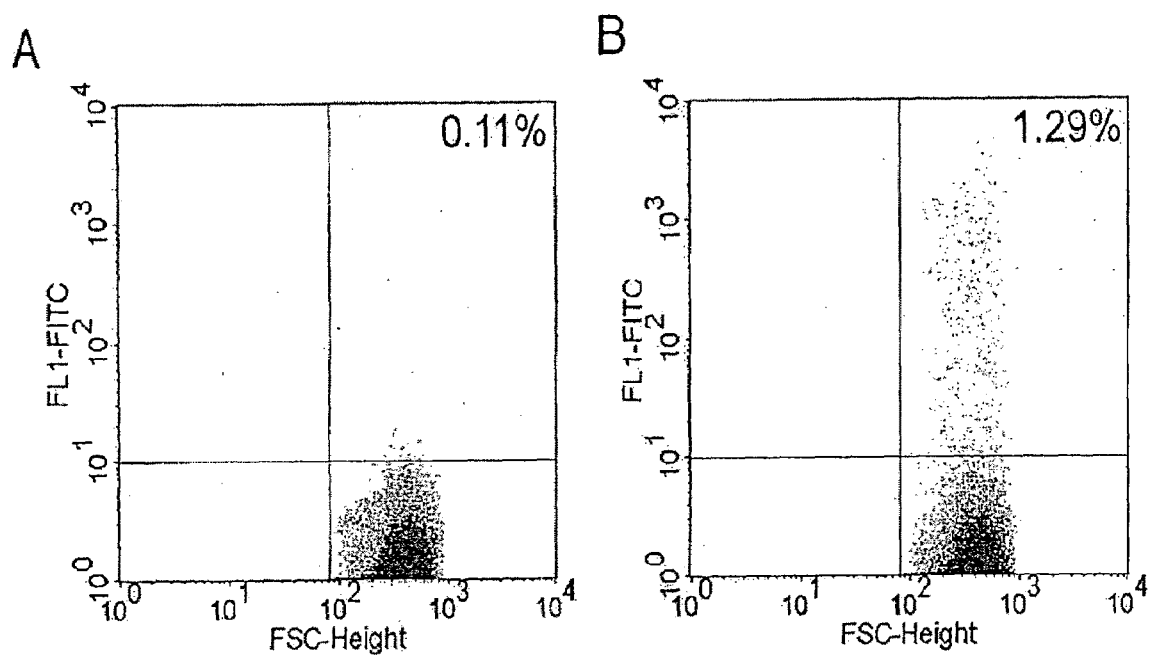

FIG. 5. Transduction of tracheal epithelial cells ("RTEC") by lentivirus vector expressing EGFP.

Representative analyses of EGFP expression as determined by FACS are shown. Differentiated RTEC were infected with VSV-G pseudotyped lentivirus vectors from the apical surface (A) without or (B) with EGTA and analyzed three days post-transduction. Delivery of lentivirus vector alone to the apical surface resulted in only rare transduced cells (A) (mean 0.14%±0.02%, n=9). Apical delivery of lentivirus vector in the presence surface of EGTA in hypotonic HEPES to access the basolateral surface significantly (P<0.05) enhanced transduction (2.11%±0.45%, n=11).

Figure 6:
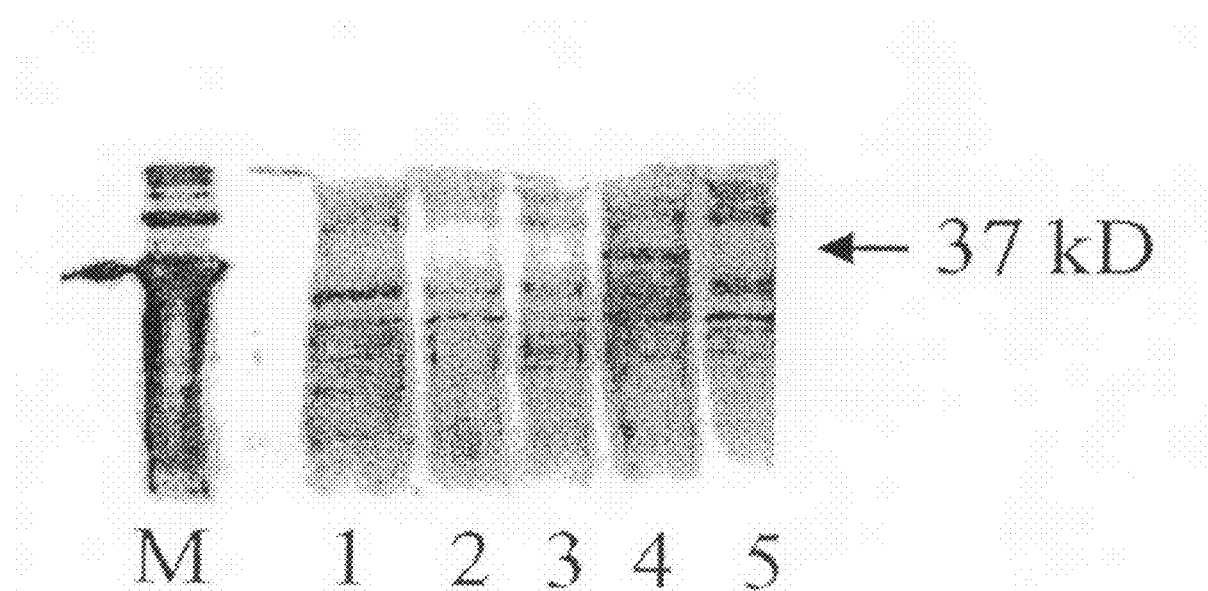

FIG. 6. GFP expression following introduction of lentivirus in vivo.

250 μl of lentivirus containing a green fluorescent protein (GFP) reporter was introduced into rat lung by tracheal instillation through a cannula wedged in the left lower lobe. Protein was harvested from lungs 48 hr following infection with lentivirus. Western blotting using an anti-GFP antibody demonstrates GFP expression as a 37 kD band in the left lower lobe (lane 4), but not in other lobes (lanes 2, 3, 5) or in lungs of non-infected animals (lane 1).

DETAILED DESCRIPTION OF THE INVENTION

All scientific terms are to be given their ordinary meanings as understood by those of skill in the art, unless an alternate meaning is set forth below. In case of conflict, the definitions set forth in this specification shall control.

A "reporter protein" is defined to mean a protein that is not normally produced in the target cell and whose presence indicates successful gene transfer from the vector to the target cell. The reporter protein may itself be the therapeutic functional protein or drug to be delivered to the target cell.

A "non-toxic dosage" is defined to mean a dosage sufficient to provide enough coverage to distribute the virus throughout the airway, but without drowning the animal or leading to other adverse events.

In the present invention, AEC in primary culture were efficiently transduced by VSV-G pseudotyped lentivirus vectors, both under culture conditions in which the cells are not actively dividing and in vivo. Transduction of AEC by lentivirus greatly exceeds that achieved with similarly pseudotyped MLV retrovirus. Furthermore, in contrast to the low levels of predominantly basolateral transduction observed in tracheal epithelial cells, the present invention achieves efficient transduction of lentivirus introduced from the apical side of polarized AEC monolayers. The present invention also successfully uses lentivirus vectors for efficient gene delivery in the distal respiratory tract in vivo.

Consistent with previous observations in other relatively quiescent cell types (e.g., neurons) (34), the present invention demonstrates that transduction of AEC with a VSV-G pseudotyped lentivirus vector is highly efficient with more than 90% of infected cells expressing GFP as determined by FACS analysis at the highest MOI. The reduction in GFP expression after transduction in the presence of AZT, together with the results of Southern analysis, make it likely that the observed GFP fluorescence reflects true transduction by the lentivirus vectors.

Transduction of AEC by lentivirus vectors greatly exceeded that achieved with similarly pseudotyped MLV vectors. Despite concentration to relatively high titers facilitated by VSV-G pseudotyping, only low-level transduction of AEC by MLV-based vectors was observed in the current study. The low level of MLV vector transduction observed in AEC is consistent with previous reports of inefficient gene transfer by amphotropic MLV vectors in quiescent airway epithelial cells from trachea and bronchi, even after disruption of epithelial tight junctions to allow basolateral access (19, 21, 31). Together, these results demonstrate the superiority of VSV-G pseudotyped lentivirus for transduction of AEC relative to a similarly pseudotyped MLV-based vector of comparable titer.

One of the important observations in gene transfer over the past decade has been that transduction is typically polarized. The apparent basolateral preference in airway epithelial cells has precluded the use of retrovirus and, additionally, has limited apical adenovirus gene transfer due, at least in part, to a preferential basolateral distribution of the adenovirus fiber protein receptors (36, 49). Although lentivirus-mediated gene transfer has the dual advantages of long-term expression by virtue of integration into the genome and transduction of quiescent cells, the vector has also been viewed as inefficient for pulmonary gene delivery due to reports of limited transduction by apically applied VSV-G-pseudotyped lentivirus vectors in the upper respiratory tract (19, 21).

Therefore, assessment of the polarity of transduction was central to the investigation of lentivirus transduction of AEC. To address this, a well-characterized model in which AEC form tight monolayers with high transepithelial resistance and exhibit polarized distribution of a variety of membrane-associated proteins (e.g., Na channel and Na pump subunits) (7, 24, 39) was used. Over a period of 3 to 4 days, isolated rate type II alveolar (AT2) cells maintained in primary culture gradually lose the characteristic hallmarks of type II cells, such as lamellar bodies and production of surfactant-associated proteins, and change morphologically to resemble alveolar type I (AT1) cells, becoming more flattened with expansive cytoplasmic processes (6). Concurrently, they begin to express a number of phenotypic markers specific for alveolar type I cells in situ, suggesting that AT2 cells in culture are undergoing transdifferentiation toward a type I cell-like phenotype (9, 10). AT2-to-AT1 cell transdifferentiation occurs in the absence of appreciable cell division (27). When grown on semipermeable supports, the cells form polarized high-resistance monolayers and exhibit active sodium transport that occurs in a vectorial fashion, similar to that observed in the alveolar epithelium in vivo (7). Previous studies have demonstrated minimal DNA synthesis in AEC cultivated in vitro at high density ($>2\times10^5$ cells/cm$^2$) in the absence of exogenous growth factors, with a nuclear labeling index consistently on the order of 1 to 3% (26, 27, 28, 46, 48). AEC in primary culture therefore constitute a well-characterized in vitro model with which to evaluate characteristics of the polarized and relatively quiescent alveolar epithelium.

In the present invention, polarized monolayers of primary AEC exhibiting high transepithelial resistance could be efficiently transduced when VSV-G-pseudotyped lentivirus vectors were introduced from the apical cell surface. In contrast, transduction of VSV-G-pseudotyped lentivirus vectors applied to the basolateral surface of AEC was markedly lower. Transduction efficiency of apically applied virus was also assessed after the addition of EGTA in order to facilitate access of the virus to the basolateral cell surface. Lack of an increase in transduction in the presence of EGTA, despite a marked reduction in $R_t$, suggests that AEC uptake of VSV-G-pseudotyped lentivirus occurs preferentially from the apical surface. By comparison, transduction of polarized RTEC by VSV-G-pseudotyped lentivirus was far lower from the apical surface and was significantly increased after disruption of tight junctions, a finding consistent with more efficient transduction from the basolateral cell surface in RTEC.

These observations in RTEC are similar to previous studies in which human bronchial or nasal airway cells in culture were 30-fold more efficiently transduced from the basolateral side by VSV-G pseudotyped lentivirus although overall efficiency of transduction was not stated (21). In that study, enhanced in vivo gene transfer efficiency to nasal and tracheal epithelium of rodents of a VSV-G pseudotyped human lentivirus vector was observed following sulfur dioxide injury, presumably by increasing access of vector to the basolateral cell surface. Similarly, Goldman et al. (19), demonstrated that lentivirus vectors pseudotyped with the VSV-G envelope were able to transduce undifferentiated airway epithelia although they failed to transduce the well-differentiated pseudostratified columnar epithelium in human bronchial xenografts. Whereas Wang et al. (51) reported that feline immunodeficiency viral vector pseudotyped with VSV-G could transduce differentiated airway epithelium in rabbits only in the presence of EGTA, Kobinger et al. (25), comparatively analyzed the effects of pseudotyping on transduction, demonstrating similar low levels of apical transduction by VSV-G pseduotyped lentivirus vectors in well-differentiated human airway epithelial cells.

Polarized gene transfer to epithelia can be mediated by a number of mechanisms including differential distribution of viral receptors on apical and basolateral cell surfaces, inactivation or inaccessibility of viral receptors, or inactivation or inhibition of virus after entry. High-resistance monolayers of Madin-Darby Canine Kidney ("MDCK") cells have previously been shown to be infected more efficiently from the basolateral cell surface by wild-type VSV (18). This has lead to the presumption that the putative receptor for wild-type VSV-G (suggested to be a phospholipid such as phosphatidylserine) (41), is located on the basolateral surface of all polarized epithelia. It has similarly been suggested that a predominant basolateral distribution of retroviral receptors in mature airway epithelia may account for limited viral entry observed from the apical side for amphotropic vectors (30, 50). However, the precise distribution (and/or function) of cellular VSV-G receptors in airway or alveolar epithelia has not been characterized and could be different among various cell types. Consistent with this notion, apical transduction of VSV-G pseudotyped lentivirus vectors has recently been demonstrated in intestinal epithelial cells (42), suggesting the presence of receptors for VSV-G on the apical cell surface in specific cell types.

In addition to reversed polarity of VSV-G receptors in AEC compared with airway epithelium or other cell types, differential intracellular trafficking or processing of virus following infection from either surface could also account for differences in transduction in polarized cells. Duan et al. (13) recently observed that in human airway epithelia, preferential basolateral transduction of adeno-associated virus could be attributed to differences in endosomal processing of apically or basolaterally internalized virions. This altered intracellular processing lead to degradation and low gene transfer of adeno-associated virus applied to the apical surface of polarized airway epithelia. Inhibition of this pathway led to an increase in apical gene delivery by more than 200-fold. The possibility that differences in the post-endocytosis processing pathways between airway and alveolar epithelium may account for the differences in apical or basolateral transduction at these two sites requires further investigation.

The adaptation of lentiviruses such as HIV for use as gene transfer vectors, while achieving high transduction efficiency in primary cells compared to standard murine retrovirus vectors, has raised concerns regarding inadvertent production of replication-competent virus. However, recent advances in lentivirus vector design have substantially reduced such concerns. The third-generation lentivirus vectors used in this study include only a very small fraction of the wild type HIV genome (57). An added safety feature introduced in the self-inactivating ("SIN") transfer vector used in this study is the deletion of U3 sequences in the 3' LTR, which is then duplicated in the 5' LTR during reverse transcription and eliminates production of full-length vector RNA (32, 57). This change further minimizes the likelihood of producing replication-competent lentivirus. Finally, since these replication-defective vectors do not themselves express any lentivirus proteins, they have not yet been noted to trigger an immune response against transduced cells in animal models (45).

The present invention demonstrates that VSV-G-pseudotyped lentivirus vectors efficiently transduce AEC in primary culture, with transduction being favored by virus application from the apical side. In contrast, transduction of RTEC by apically applied lentivirus was negligible. Transduction efficiency in AEC increased with increasing MOI and greatly exceeded that achieved with a similarly pseudotyped MLV retrovirus vector. The present invention also demonstrates the successful transfer of genes through lentivirus vector transduction. Mammals injected with lentivirus vector into the trachea expressed measurable quantities of the reporter protein within 48 to 72 hours after infection. No adverse events including respiratory distress or histological evidence of acute inflammation were noted in the lungs.

EXAMPLE I

Lentivirus Vector for Gene Transfer to Alveolar Epithelial Cells

Figure 1:
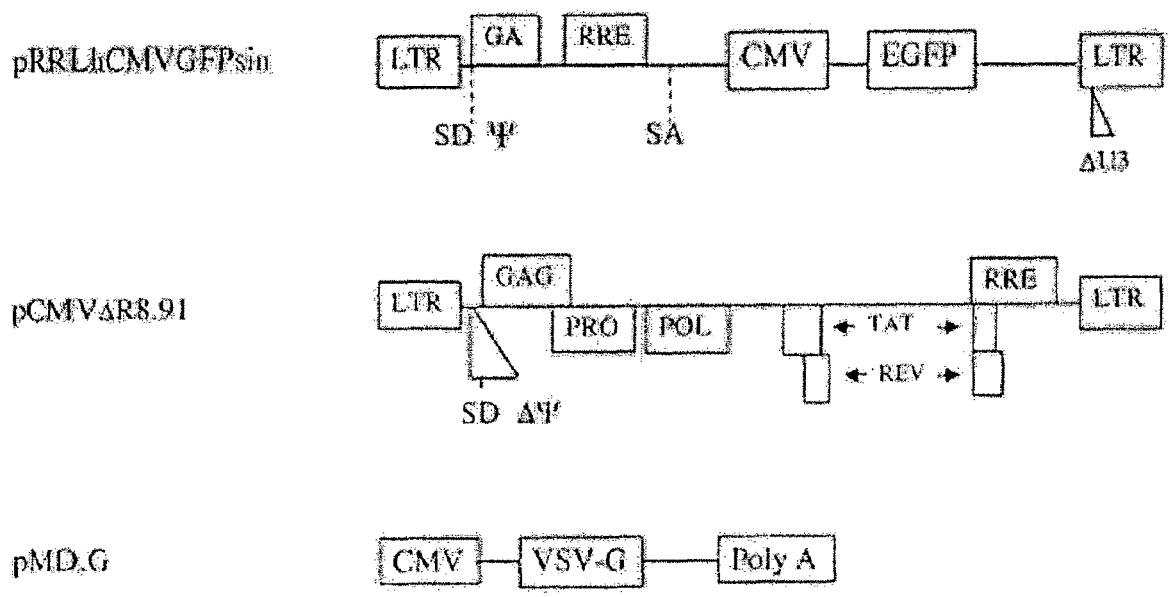
FIG. 1. Vectors used for generation of lentivirus.

Recombinant lentivirus vector and packaging constructs were generously provided by Dr. L. Naldini (University of Torino, Italy) and produced as described in (34). A self-inactivating replication defective human lentiviral (HIV) transfer vector expressing enhanced green fluorescent protein (EGFP) from the cytomegalovirus (CMV) immediate early promoter was used. Human 293T cells were co-transfected with calcium phosphate precipitation at 80-90% confluence with 12 μg pRRLsin.hCMVGFP, 10 μg pCMVΔR8.91 for viral packaging and 8 μg pMD.G for VSV-G pseudotyping. The vectors used for generation of lentivirus are shown in FIG. 1. Virus was isolated and for some experiments was concentrated through a Macrosep™ centrifugal concentrator (Pall, Gelman Sciences, MI) with a 300 kDa molecular weight cutoff and stored at −80° C. Vector stocks were tittered on HeLa cells by flow cytometry and were in the range of $10^6$-$10^8$ TU/ml. MLV-based vectors were generated using a similar protocol and similarly pseuodotyped with VSV-G.

EXAMPLE II

In Vitro Transduction of Alveolar Epithelial Cells Using Lentivirus

Rat Alveolar Epithelial Cell Isolation and Culture

Type II (AT2) cells were isolated from adult male Sprague Dawley rats by disaggregation with elastase (2.0-2.5 U/ml) (Worthington Biochemical, Freehold, N.J.) followed by panning on IgG-coated bacteriologic plates. Enriched AT2 cells were resuspended in growth medium (MDSF) comprised of Dulbecco's modified Eagle's medium and Ham's F12 nutrient mixture in a 1:1 ratio (DMEF-12: Sigma Chemical, St Louis, Mo.), supplemented with 1.25 mg/ml bovine serum albumin (BSA) (Collaborative Research, Bedford, Mass.), 10 mM Hepes, 0.1 mM nonessential amino acids, 2.0 mM glutamine, 100 U/ml sodium penicillin G, and 100 μg/ml streptomycin and 10% newborn bovine serum (Omega Scientific, Tarzana, Calif.). Cells were seeded onto plastic, chamber slides or tissue culture-treated polycarbonate (Nuclepore) filter cups (0.4 μm pore size, 1.1 cm² diameter; Transwell; Corning-Costar, Cambridge, Mass.) at a density of $1.0 \times 10^6$ cells/cm² and grown to confluence. Media were changed on the second day after plating and every other day thereafter. Cultures were maintained in a humidified 5% $CO_2$ incubator at 37° C. AT2 cell purity (>90%) was assessed by staining freshly isolated cells for lamellar bodies with tannic acid. Cell viability (>90%) was measured by trypan blue dye exclusion.

Rat Tracheal Epithelial Cell Isolation and Culture

Rat trachea epithelial cells (RTEC) were isolated from adult male Sprague Dawley rats by incubation of tracheas overnight at 4° C. in 0.15% pronase (Roche Molecular Biochemicals, Indianapolis, Ind.). Tracheas were agitated to release cells then incubated in DNase I (0.5 mg/ml, 5 min on ice). Cells were adhered (2 h) to remove fibroblasts, and non-adherent cells were counted and viability determined by exclusion of trypan blue (>90% viable). RTEC were resuspended in defined media consisting of DMEM/Ham's F12 (1:1 ratio) supplemented with L-glutamine (6.5 mM), NaHCO3 (0.12%), insulin (10 μg/ml), hydrocortisone (0.1 μg/ml), transferrin (5 μg/ml), phosphoethanolamine (50 μM), ethanolamine (80 μM), cholera toxin (0.1 μg/ml), bovine pituitary extract (0.03 mg/ml), HEPES (30 mM), BSA (0.5 mg/ml), retinoic acid (0.05 μM), penicillin (50 U/ml), streptomycin (50 μg/ml), and fungizone (0.25 μg/ml) as described by others (22, 35). EGF 10 ng/ml (Becton Dickinson Labware, Bedford, Mass.) was previously titrated to maximize the number of ciliated cells. Cells were seeded ($5 \times 10^5$ cells/cm²) onto 0.33 cm² polyester membranes (0.4 μM pore size; Transwell Clear, Corning-Costar) coated with rat tail collagen (50 μg/ml) (Becton Dickinson Labware) and incubated at 37° C. supplemented with 5% $CO_2$. Nuserum (10%; Becton Dickinson Labware) was added during the first two days. Cells were maintained with media in the upper and lower chambers until transmembrane resistance was greater than 300 Ω/cm², indicating tight junction formation. Media was then removed from the apical chamber (typically at days 2 to 4) and cells were maintained at air liquid interface (ALI) by daily supplying fresh media to the basolateral chamber only. Differentiated, multi-layered epithelial cell populations were assessed by histology of paraffin embedded sections of membranes.

Measurement of Bioelectric Properties

Transepithelial resistance ($R_t$) and spontaneous potential difference (SPD) of AEC and tracheal epithelial cells grown on filters were measured using a rapid screening device (Millicell-ERS, Millipore, Bedford, Mass.) as previously described. Short-circuit current ($I_{SC}$) was calculated from the relationship $I_{SC}=SPD/R_t$. Cell culture media and all other chemicals were purchased from Sigma Chemical and were of the highest commercial purity available.

Vector Production and Virus Preparation

The lentivirus vectors were produced as described in Example I above.

Assessment of Alveolar Epithelial Cell Proliferation

On day 4; AEC grown on plastic in MDSF plus 10% new bovine serum were labeled with bromode-oxyuridine (BrdU; 10 μM), a thymidine analog that is incorporated into newly synthesized DNA, for 6 h. Cells were washed two times with phosphate-buffered saline (PBS), released by incubation for ten minutes at 5 μM EDTA, and washed again with PBS. Cells were fixed, permeabilized, refixed and heated with DNase by using the BrdU flow kit protocol (BD Phamingen, San Diego, Calif.). Samples were stained with a fluorescein isothiocyanate (FITC) conjugated anti-BrdU antibody and analyzed by fluorescence-activated cell sorting (FACS).

Viral Transduction of AEC

AEC grown on plastic or chamber slides were infected with lentivirus (multiplicity of infection (MOI) of 0.1 to 50) on day 4. Medium was aspirated and cells were incubated with virus for 1 hr in the presence of polybrene (8 μg/ml). Cells were trypsinized 72 hr after transduction, washed, and resuspended in phosphate buffered saline (PBS). Efficiency of cell transduction was analyzed by FACS using a Becton-Dickinson FACScan with a 488 nm argon laser. To confirm that GFP expression was not the result of pseudotransduction, control experiments were performed in the presence of zidovudine (AZT; 200 μM) to inhibit viral reverse transcriptase. Efficiency of transduction of AEC by VSV-G pseudotyped lentivirus or MLV-based virus of comparable titers were compared and analyzed in a similar fashion. Live gating of viable cells was performed by using forward-scatter and side-scatter parameters, and the percent of cells exhibiting EGFP fluorescence was quantified on fluorescence channel 1 (FL1).

Assessment of Polarity of Lentiviral Entry into Alveolar Epithelial Cells

To assess the polarity of lentiviral entry into AEC, on day 4, confluent polarized AEC monolayers (transepithelial resistance ($R_t$)>2 k$\Omega$/cm$^2$) grown on tissue culture-treated polycarbonate filters were incubated with concentrated lentivirus applied either to the apical or basolateral cell surface for 1 hr at 37° C. $R_t$ was measured 30 min. before, 30 min. and 3 days after infection. For infection from the apical side, media were aspirated off and cells were incubated with 100 μl of virus. For basolateral infection, media were aspirated off and the filter inverted before addition of 40 μl concentrated virus.

To investigate whether interruption of tight junctions would facilitate entry of apically applied lentivirus by increasing access to the basolateral cell surface, EGTA was first added to a final concentration of 4.5 mM followed by addition of virus to the apical side as above. Cells on filters at 72 h post-infection were rinsed with PBS, trypsinized, washed and resuspended in PBS. To ensure cell recovery, filters were also flushed one time with PBS. Transduction efficiency following infection from either apical or basolateral surface was assessed by FACS analysis.

Southern Analysis of Transduced AEC

Genomic DNA was harvested from AEC 72 h posttransduction by proteinase K digestion and phenol-chloroform extraction. A 10 μg portion was digested overnight with NotI, which yields a 2.2-kb internal fragment that encompasses EGFP, and then separated by agarose gel electrophoresis. After alkali denaturation, gels were transferred to Pall Biodyne B nylon membranes (Pall Biosupport Division, Port Washington, N.Y.) in 20×SSC (1×SSC is 0.15 M NaCl plus 0.015 M sodium citrate) buffer. A 1.1-kb DNA probe specific for EGFP was labeled by using a random primer DNA biotinylation kit (Kirkegaard & Perry Laboratories, Inc., Gaithersburg, Md.) and hybridized to the membranes in formamide hybridization buffer. Membranes were washed at high stringency, followed by incubation with alkaline phosphatase-streptavidin conjugate. After the washing, signal was detected by incubation with CDP-Star chemiluminescent substrate (Tropix, Inc., Bedford, Mass.) and exposure to X-ray film.

Viral Transduction of RTEC.

Cells grown on membranes maintained at ALI for two to four weeks were transduced by the apical or basolateral route. Proximal airway epithelial cells cultured by this method have been previously shown to be quiescent. Lentivirus (MOI approximately 5) in DMEM with polybrene (8 μg/ml) was added, incubated for 2 h, then washed off. To transduce by the basolateral route, the Transwell cups were inverted and the treatment was applied to the basal aspect of the membrane. The cup remained inverted during treatment and virus exposure, was then washed and returned to the normal orientation. To disrupt cell-cell junctions, cells were pretreated with EGTA in hypotonic solution (6 mM in 10 mM HEPES, pH 7.4) as previously described. $R_t$, was measured following EGTA treatment, lentivirus application, and daily post-infection. Media was changed daily. After three days, GFP expression was photographed under inverted fluorescence microscopy. Cells were then treated with trypsin and EDTA (Cell Dissociation Solution, Sigma) and gently pipetted several times, washed, retreated with Cell Dissociation Solution, titurated again, passed through a needle, and assayed for GFP using fluorescent activated cell sorting by FACS analysis.

Confocal Microscopy

AEC grown on chamber slides (Lab-Tek II, Nalge Nunc, Rochester, N.Y.) were infected with lentivirus on day 4. 72 hr after transduction, cells were rinsed, fixed in 2% paraformaldehyde and mounted (ProLong Antifade Kit, Molecular Probes, Oregon). Cells were viewed with a PCM 2000 slide system (Nikon USA, Melville, N.Y.).

Statistical Analysis

Data are presented as mean ±SEM of at least three separate experiments. Within an experiment, each transfection condition was performed in triplicate.

Results: Lentivirus Vectors Achieve Efficient Transduction of Alveolar Epithelial Cells A third-generation self-inactivating (SIN) lentiviral transfer vector encoding the enhanced GFP (EGFP) marker gene was packaged by a standard 3-plasmid co-transfection procedure (34) to produce vectors pseudotyped with the VSV-G envelope (FIG. 1). The titers of unconcentrated vector supernatants generated by this procedure are typically on the order of $1\times10^6$ transducing units (TU) per ml when titered on 293T or HeLa cells. After concentration, titers on the order of 108 TU 1 ml were achieved. These vectors were used to transduce rat AEC in primary culture on day 4 post-isolation, after the AT2 cells grown on tissue culture-treated plastic surfaces had progressed towards an AT1 cell-like phenotype. Under these conditions the cells are largely quiescent. FACS analysis demonstrated that only 1.0%±0.1% of cells were labeled with Brd U. Nevertheless, confocal microscopy of AEC grown on chamber slides demonstrates strong expression of EGFP three days post-transduction in a majority of cells (FIG. 2A). Representative FACS analysis three days post-transduction shows a shifted population of cells exhibiting higher fluorescence intensity specifically in the GFP wavelength (FL1 channel) with 99% GFP-positive cells, further demonstrating that AEC are efficiently transduced (FIG. 2B). Changing the plating density of AEC did not affect the percentage of GFP-positive cells after incubation with the same preparation of lentivirus, indicating that cell density has little effect on transduction efficiency (data not shown). Comparison with VSV-G pseudotyped standard MLV-based retrovirus of comparable titer demonstrates ~30-fold greater transduction by the lentivirus vector (FIG. 2C). A decrease in the number of GFP-expressing cells was observed after transduction by lentivirus vectors in the presence of AZT (~75% inhibition at 200 μM AZT), confirming that GDP expression is not due to pseudotransduction.

Dose Dependent Transduction of Alveolar Epithelial Cells by Lentivirus Vectors

To determine whether varying the MOI would alter the efficiency of gene delivery by the lentivirus vectors, fixed numbers of AEC in primary culture were plated and replicate plates were subsequently challenged with increasing dosages of the vectors. For this experiment, lentivirus vector supernatants were first concentrated by ultracentrifugation, and the titer of the concentrated vector preparation as determined by FACS analysis of transduced HeLa cells was found to be in the range of $1-2\times10^8$ TU/ml. A dose-dependent increase in transduction efficiency was observed with increasing MOI, with the GFP-positive population ranging from 4% to 99% after infection at MOIs from 0.1 to 50, respectively (FIG. 3). Although transduction of AEC by VSV-G pseudotyped lentivirus vectors is thus somewhat less efficient than transduction of HeLa cells, almost complete transduction could be achieved by increasing the MOI. No toxicity was noted at higher MOI as reflected by lack of change in morphology or cell number and the absence of a subpopulation of dead cells observed by FACS analysis.

AEC Monolayers are Transduced by VSV-G Pseudotyped Lentivirus Vectors from the Apical Surface The ability of VSV-G pseudotyped lentivirus vectors to transduce polarized monolayers of primary AEC was examined. It has previously been demonstrated that primary AEC grown on permeable filter membranes can form monolayers with intact intercellular tight junctions and exhibit high transepithelial electrical resistance (7). The $R_t$ of confluent AEC monolayers prior to infection on day 4 was measured in all experiments and was consistently found to be >2.5 $k\Omega/cm^2$, reflecting the formation of tight junctions.

To determine whether transduction of AEC occur in a polarized fashion, AEC monolayers were infected with VSV-G pseudotyped lentivirus from either the apical or basolateral side and analyzed by FACS three days post-transduction (FIG. 4A). Unexpectedly, VSV-G pseudotyped lentivirus vectors were preferentially transduced from the apical surface with an efficiency of 31±2% at an MOI of 10 (FIG. 4B). Transduction from the apical side was ~25-fold higher than when the virus was introduced from the basolateral surface. $R_t$ before and following infection is shown in Table I. Despite a reduction in $R_t$ to <0.25 $k\Omega/cm^2$, following addition of EGTA there was no increase in transduction of apically introduced virus.

TABLE 1

| $R_t$ (kA-cm2) | Control | Apical | Basolateral |
|---|---|---|---|
| 30 min. pre | 3.71 ± 0.22 | 3.78 ± 0.24 | 3.81 ± 0.19 |
| 30 min. post | 2.75 ± 0.92 | 2.07 ± 0.46 | 1.64 ± 0.55 |
| 72 hr. post | 2.66 ± 0.24 | 2.66 ± 0.34 | 2.47 ± 0.33 |

Transduction of Tracheal Epithelial Cell is from the Basolateral Surface

The polarity and efficiency of lentivirus transduction in AEC was next compared to RTEC. In contrast to the current observations in AEC, human tracheal bronchial cells have previously been shown to be preferentially transduced from the basolateral surface (19, 21). Lentivirus transduction (MOI ~5) was evaluated in differentiated RTEC maintained at air-liquid interface (ALI) for three to four weeks that had a mean transepithelial cell resistance of 847.8±16.04 $\Omega/cm^2$ indicating the establishment of tight junctions. In some experiments, EGTA was used as a pretreatment to disrupt cell-cell junctions in transfections. Apical transduction, in the absence of EGTA resulted in a rare GFP expressing cell as shown in FIG. 5 (mean 0.14±0.02%). To access the basolateral surface via apical application of lentivirus, cells were pretreated with EGTA. Following EGTA treatment, mean resistance fell to 4.4±0.69 $K/cm^2$ and remained low (13.6±1.34 $\Omega/cm^2$) after lentivirus application. The total number of GFP expressing cells at 72 h was relatively small (2.11±0.45%); however, GFP expressing cells were easily detectable. There was no detectable transduction, (with or without EGTA treatment) when lentivirus was added to the basal membrane. This was likely related to an inability of the virus to pass through the membrane and dense collagen coating required to support RTEC differentiation. Thus, the polarity of transduction of RTEC is the opposite of AECs and the efficiency of RTEC transduction is markedly below that observed in AEC.

EXAMPLE III

In Vivo Gene Transfer Through Lentivirus Vector Transduction in Mammalian AEC

Adult rats were anesthetized by ketamine/xylazine administered intramuscularly. Vocal cords were visualized using an ear-piece attached to an otoscope. A flexible catheter (diameter 1.2 mm) was inserted into the trachea under direct visualization. 250 µl lentivirus vector containing GFP or saline solution was injected followed by 0.5 cc air bolus into the lungs. The animals were wrapped in a warm blanket and allowed to recover. Food and water were provided ad lib. 48-72 h later, animals were sacrificed and the lungs were harvested to analyze expression of a GFP reporter gene by immunocytochemistry, mRNA and protein analysis.

Immunohistochemistry and western analysis (FIG. 6) illustrate that the reporter protein was expressed in the lungs of rats infected with the lentivirus.

REFERENCES

1. Albelda, S. M., R. Wiewrodt, and J. B. Zuckerman. 2000. Gene therapy for lung disease: hype or hope? Ann. Intern. Med. 132:649-660.
2. Bertalanffy F. D. 1964. Respiratory tissue: structure, histophysiology, cyto-dynamics. II. New approaches and interpretations. Int. Rev. Cytol. 17:213-297.
3. Borok, Z., S. I. Danto, S. M. Zabski, and E. D. Crandall. 1994. Defined medium for primary culture de novo of adult rat alveolar epithelial cells. In Vitro Cell Dev. Biol. Anim. 30A:99-104.
4. Bowden, D. H., E. Davies, and J. P. Wyatt. 1968. Cytodynamics of pulmonary alveolar cells in the mouse. Arch. Pathol. 86:667-670.
5. Brigham, K. L., and A. A. Stecenko. 2000. Gene therapy for acute lung injury. Intensive Care Med. 26:S119-S123.
6. Cheek, J. M., M. J. Evans, and E. D. Crandall. 1989. Type I cell-like morphology in tight alveolar epithelial monolayers. Exp. Cell Res. 184:375-387.
7. Cheek, J. M., K. J. Kim, and E. D. Crandall. 1989. Tight monolayers of rat alveolar epithelial cells: bioelectric properties and active sodium transport. Am. J. Physiol. 256:C688-C693.
8. Chirmule, N., K. Propert, S. Magosin, Y. Qian, R Qian, and J. Wilson. 1999. Immune responses to adenovirus and adeno-associated virus in humans. Gene Ther. 6:1574-1583.
9. Christensen, P. J., S. Kim, R. H. Simon, G. B. Toews, and R D. Paine. 1993. Differentiation-related expression of ICAM-1 by rat alveolar epithelial cells. Am. J. Respir. Cell Mot. Biol. 8:9-15.
10. Danto, S. I., S. M. Zabski, and E. D. Crandall. 1992. Reactivity of alveolar epithelial cells in primary culture with type I cell monoclonal antibodies. Am. J. Respir. Cell Mol. Biol. 6:296-306.

11. Dobbs, L. G., R. Gonzalez, and M. C. Williams. 1986. An improved method for isolating type II cells in high yield and purity. Am. Rev. Respir. Dis. 134:141-145.
12. Dong, J. Y., D. Wang, F. W. Van Ginkel, D. W. Pascual, and R A. Frizzell. 1996. Systematic analysis of repeated gene delivery into animal lungs with a recombinant adenovirus vector. Hum. Gene Ther. 7:319-331.
13. Duan, D., Y. Vue, Z. Yan, J. Yang, and J. F. Engelhardt. 2000. Endosomal processing limits gene transfer to polarized airway epithelia by adeno-associated virus. J. Clin. Investig. 105:1573-1587.
14. Engelhardt, J. F., J. R. Yankaskas, and J. M. Wilson. 1992. In vivo retroviral gene transfer into human bronchial epithelia of xenografts. J. Clin. Investig. 90:2598-2607.
15. Factor, P., F. Saldias, K. Ridge, V. Dumasius, J. Zabner, H. A. Jaffe, G. Blanco, M. Barnard, R. Mercer, R. Perrin, and J. I. Sznajder. 1998. Augmentation of lung liquid clearance via adenovirus-mediated transfer of a Na,K-ATPase beta 1 subunit gene. J. Clin. Investig. 102:1421-1430.
16. Flotte, T. R, S. A. Afione, C. Conrad, S. A. McGrath, R. Solow, H. Oka, P. L. Zeitlin, W. B. Guggino, and B. J. Carter. 1993. Stable in vivo expression of the cystic fibrosis transmembrane conductance regulator with an adeno-associated virus vector. Proc. Natl. Acad. Sci. USA 90:10613-10617.
17. Flotte, T. R, S. A. Afione, and P. L. Zeitlin. 1994. Adeno-associated virus vector gene expression occurs in nondividing cells in the absence of vector DNA integration. Am. J. Respir. Cell Mol. Biol. 11:517-521.
18. Fuller, S., C. H. von Bonsdorff, and K. Simons. 1984. Vesicular stomatitis virus infects and matures only through the basolateral surface of the polarized epithelial cell line, MDCK. Cell 38:65-77.
19. Goldman, M. J., P. S. Lee, J. S. Yang, and J. M. Wilson. 1997. Lentivirus vectors for gene therapy of cystic fibrosis. Hum. Gene Ther. 8:2261-2268.
20. Grimm, D., and J. A. Kleinschmidt. 1999. Progress in adeno-associated virus type 2 vector production: promises and prospects for clinical use. Hum. Gene Ther. 10:2445-2450.
21. Johnson, L. G., J. C. Olsen, L. Naldini, and R C. Boucher. 2000. Pseudotyped human lentivirus vector-mediated gene transfer to airway epithelia in vivo. Gene Ther. 7:568-574.
22. Kaartinen, L., P. Nettesheim, K. B. Adler, and S. H. Randell. 1993. Rat tracheal epithelial cell differentiation in vitro. In Vitro Cell Dev. Biol. Anim. 29A:481-492.
23. Kafri, T., U. Blomer, D. A. Peterson, F. H. Gage, and I. M. Verma. 1997. Sustained expression of genes delivered directly into liver and muscle by lentivirus vectors. Nat. Genet. 17:314-317.
24. Kim, K. J., J. M. Cheek, and E. D. Crandall. 1991. Contribution of active Na$^+$ and Cl$^-$ fluxes to net ion transport by alveolar epithelium. Respir. Physiol. 85:245-256.
25. Kobinger, G. P., D. J. Weiner, Q. C. Yu, and J. M. Wilson. 2001. Filovirus-pseudotyped lentivirus vector can efficiently and stably transduce airway epithelia in vivo. Nat. Biotechnol. 19:225-230.
26. Leslie, C. C., K. McCormick-Shannon, J. L. Cook, and R. J. Mason. 1985. Macrophages stimulate DNA synthesis in rat alveolar type II cells. Am. Rev. Respir. Dis. 132:1246-1252.
27. Leslie, C. C., K. McCormick-Shannon, P. C. Robinson, and R. J. Mason. 1985. Stimulation of DNA synthesis in cultured rat alveolar type II cells. Exp. Lung Res. 8:53-66.
28. Leslie, C. C., K. McCormick-Shannon, J. M. Shannon, B. Garrick, D. Damm, J. A. Abraham, and R. J. Mason. 1997. Heparin-binding EGF-like growth factor is a mitogen for rat alveolar type II cells. Am. J. Respir. Cell Mol. Biol. 16:379-387.
29. Mason, R. J., S. R. Walker, B. A. Shields, J. E. Henson, and M. C. Williams. 1985. Identification of rat alveolar type II epithelial cells with a tannic acid and polychrome stain. Am. Rev. Respir. Dis. 131:786-788.
30. Miller, A. D. 1996. Cell-surface receptors for retroviruses and implications for gene transfer. Proc. Natl. Acad. Sci. USA 93:11407-11413.
31. Miller, D. G., M. A. Adam, and A. D. Miller. 1990. Gene transfer by retrovirus vectors occurs only in cells that are actively replicating at the time of infection. Mol. Cell. Biol. 10:4239-4242.
32. Miyoshi, H., U. Blomer, M. Takahashi, F. H. Gage, and I. M. Verma. 1998. Development of a self-inactivating lentivirus vector. J. Virol. 72:8150-8157.
33. Naldini, L. 1998. Lentiviruses as gene transfer agents for delivery to non-dividing cells. Curr. Opin. Biotechnol. 9:457-463.
34. Naldini, L., U. Blomer, P. Gallay, D. Ory, R. Mulligan, F. H. Gage, I. M. Verma, and D. Trono. 1996. In vivo gene delivery and stable transduction of nondividing cells by a lentivirus vector. Science 272:263-267.
35. Ostrowski, L. E., S. H. Randell, A. B. Clark, T. E. Gray, and P. Nettesheim. 1995. Ciliogenesis of rat tracheal epithelial cells in vitro. Methods Cell Biol. 47:57-63.
36. Pickles, R. J., D. McCarty, H. Matsui, P. J. Hart, S. H. Randell, and R C. Boucher. 1998. Limited entry of adenovirus vectors into well-differentiated airway epithelium is responsible for inefficient gene transfer. J. Virol. 72: 6014-6023.
37. Polonovsky, V., and P. B. Bitterman. 1997. Regulation of cell population size, p. 133-144. In J. B. West and R. G. Crystal (ed:), The lung: scientific foundations, 2nd ed., vol. 1. Lippincott-Raven Publishers, Philadelphia, Pa.
38. Reiser, J. 2000. Production and concentration of pseudotyped HIV-1-based gene transfer vectors. Gene Ther. 7:910-913.
39. Russo, R M., R. L. Lohman, and E. D. Crandall. 1992. Evidence for amiloride-sensitive sodium channels in alveolar epithelial cells. Am. J. Physiol. 262:L405-L411.
40. Sakoda, T., N. Kasahara, Y. Hamamori, and L. Kedes. 1999. A high-titer lentiviral production system mediates efficient transduction of differentiated cells including beating cardiac myocytes. J. Mol. Cell. Cardiol. 31:2037-2047.
41. Schlegel, R, T. S. Tralka, M. C. Willingham, and I. Pastan. 1983. Inhibition of VSV binding and infectivity by phosphatidylserine: is phosphatidylserine a VSV-binding site? Cell 32:639-646.
42. Seppen, J., S. C. Barry, J. H. Klinkspoor, L. J. Katen, S. P. Lee, J. V. Garcia, and W. R Osborne. 2000. Apical gene transfer into quiescent human and canine polarized intestinal epithelial cells by lentivirus vectors. J. Virol. 74:7642-7645.
43. Sisson, T. H., N. Hattori, Y. Xu, and R. H. Simon. 1999. Treatment of bleomycin-induced pulmonary fibrosis by transfer of urokinase-type plasminogen activator genes. Hum. Gene Ther. 10:2315-2323.
44. Soneoka, Y., P. M. Cannon, E. E. Ramsdale, J. C. Griffiths, G. Romano, S. M. Kingsman, and A. J. Kingsman. 1995. A transient three-plasmid expression system for the production of high titer retroviral vectors. Nucleic Acids Res. 23:628-633.
45. Trono, D. 2000. Lentivirus vectors: turning a deadly foe into a therapeutic agent. Gene Ther. 7:20-23.

46. Uhal, B. D. 1997. Cell cycle kinetics in the alveolar epithelium. Am. J. Physiol. 272:L1031-L1045.
47. Uhal, B. D., and M. D. Etter. 1993. Type II pneumocyte hypertrophy without activation of surfactant biosynthesis after partial pneumonectomy. Am. J. Physiol. 264:L153-L159.
48. Uhal, B. D., and D. E. Rannels. 1991. DNA distribution analysis of type II pneumocytes by laser flow cytometry: technical considerations. Am. J. Physiol. 261:L296-L306.
49. Walters, R W., T. Grunst, J. M. Bergelson, R. W. Finberg, M. J. Welsh, and J. Zabner. 1999. Basolateral localization of fiber receptors limits adenovirus infection from the apical surface of airway epithelia. J. Biol. Chem. 274:10219-10226.
50. Wang, G., B. L. Davidson, P. Melchert, V. A. Slepushkin, H. H. van Es, M. Bodner, D. J. Jolly, and P. B. McCray. 1998. Influence of cell polarity on retrovirus-mediated gene transfer to differentiated human airway epithelia. J. Virol. 72:9818-9826.
51. Wang, G., V. Slepushkin, J. Zabner, S. Keshavjee, J. C. Johnston, S. L. Sauter, D. J. Jolly, T. W. Dubensky, Jr., B. L. Davidson, and P. B. McCray, Jr. 1999. Feline immunodeficiency virus vectors persistently transduce nondividing airway epithelia and correct the cystic fibrosis defect. J. Clin. Investig. 104:R55-R62.
52. Wang, G., V. A. Slepushkin, M. Bodner, .J. Zabner, H. H. van Es, P. Thomas, D. J. Jolly, B. L. Davidson, and P. B. McCray. 1999. Keratinocyte growth factor induced epithelial proliferation facilitates retroviral-mediated gene transfer to distal lung epithelia in vivo. J. Gene Med. 1:22-30.
53. Wang, G., J. Zabner, C. Deering, J. Launspach, J. Shao, M. Bodner, D. J. Jolly, B. L. Davidson, and P. B. McCray, Jr. 2000. Increasing epithelial junction permeability enhances gene transfer to airway epithelia in vivo. Am. J. Respir. Cell Mol. Biol. 22:129-138.
54. Welsh, M. J. 1999. Gene transfer for cystic fibrosis. J. Clin. Investig. 104:1165-1166.
55. Yang, Y., Q. Li, H. C. Ertl, and J. M. Wilson. 1995. Cellular and humoral immune responses to viral antigens create barriers to lung-directed gene therapy with recombinant adenoviruses. J. Virol. 69:2004-2015.
56. Zabner, J. 1997. Cationic lipids used in gene transfer. Adv. Drug Deliv. Rev. 27:17-28.
57. Zufferey, R., T. Dull, R. J. Mandel, A. Bukovsky, D. Quiroz, L. Naldini, and D. Trono. 1998. Self-inactivating lentivirus vector for safe and efficient in vivo gene delivery. J. Virol. 72:9873-9880.
58. Zufferey, R., D. Nagy, R J. Mandel, L. Naldini, and D. Trono. 1997. Multiply attenuated lentivirus vector achieves efficient gene delivery in vivo. Nat. Biotechnol. 15:871-875

We claim:

1. A method for in vitro transduction of alveolar epithelial cells using vesicular stomatitis virus envelope glycoprotein (VSV-G) pseudotyped lentivirus vector comprising:
    a. isolating said alveolar epithelial cells (AEC);
    b. developing a culture of said AEC;
    c. preparing said lentivirus vector;
    d. infecting more than 90% of said AEC with said lentivirus vector; and
    e. trypsinizing said AEC approximately after infecting.
2. The method of claim 1 wherein the alveolar epithelial cells are mammalian.

* * * * *